United States Patent
Hete et al.

(10) Patent No.: US 6,708,690 B1
(45) Date of Patent: Mar. 23, 2004

(54) APPARATUS AND METHOD FOR PROVIDING HIGH FREQUENCY VARIABLE PRESSURE TO A PATIENT

(75) Inventors: Bernie F. Hete, Trafford, PA (US); Michael Bobeck, Sarver, PA (US)

(73) Assignee: Respironics, Inc., Murrysville, PA (US)

( * ) Notice: Subject to any disclaimer, the term of this patent is extended or adjusted under 35 U.S.C. 154(b) by 251 days.

(21) Appl. No.: 09/652,747

(22) Filed: Aug. 31, 2000

Related U.S. Application Data

(60) Provisional application No. 60/152,441, filed on Sep. 3, 1999.

(51) Int. Cl.[7] .............................................. A61M 16/00
(52) U.S. Cl. ............................ 128/204.18; 128/204.21; 128/205.24
(58) Field of Search ...................... 128/204.18, 204.21, 128/205.24, 911, 205.18; 137/908

(56) References Cited

U.S. PATENT DOCUMENTS

| | | | |
|---|---|---|---|
| 4,592,349 A | 6/1986 | Bird | |
| 5,007,420 A | 4/1991 | Bird | |
| 5,056,505 A | * 10/1991 | Warwick et al. | ............... 601/44 |
| 5,555,880 A | 9/1996 | Winter et al. | |
| 5,630,411 A | * 5/1997 | Holscher | ............... 128/205.24 |
| 5,746,199 A | 5/1998 | Bayron et al. | |
| 5,850,835 A | 12/1998 | Takaki et al. | |
| 5,862,802 A | 1/1999 | Bird | |
| 5,871,008 A | 2/1999 | Poon et al. | |
| 5,931,163 A | 8/1999 | Stegmann et al. | |
| 5,988,166 A | * 11/1999 | Hayek | ................... 128/205.26 |
| 6,066,101 A | 5/2000 | Johnson et al. | |
| 6,142,952 A | * 11/2000 | Behbehani et al. | ......... 600/533 |
| 6,182,656 B1 | 2/2001 | Sagiv | |
| 6,209,540 B1 | * 4/2001 | Sugiura et al. | ........ 128/204.18 |
| 6,446,629 B1 | * 9/2002 | Takaki et al. | .......... 128/204.18 |

* cited by examiner

Primary Examiner—Aaron J. Lewis
Assistant Examiner—Mital Patel
(74) Attorney, Agent, or Firm—Michael W. Haas

(57) ABSTRACT

A high frequency pressure oscillation device and method of providing high frequency pressure oscillations to a patient. The device includes a patient circuit coupling a gas source to an airway of a patient, and a valve disposed in the patient circuit. The valve communicates the gas source with the patient's airway when in a first position and at least partially restricts communication when in a second position. A rotating drive assembly rotates the valve in a first direction such that the valve is alternatively disposed in the first and second positions. This system is capable of delivering positive and negative pressures to the airway of a patient by including a blower as the source of breathing gas. This system is also capable of superimposing a high frequency oscillating pressure signal on another pressure signal by adding a second blower in series with the first blower.

7 Claims, 10 Drawing Sheets

APPARATUS AND METHOD FOR PROVIDING HIGH FREQUENCY VARIABLE PRESSURE TO A PATIENT

This application claims the benefit of Provisional Application Ser. No. 60/152,441 filed Sep. 3, 1999.

BACKGROUND OF THE INVENTION

1. Field of the Invention

The present invention pertains to an apparatus and method for providing high frequency variable pressure to a patient to treat a respiratory disorder, and, in particular, to an apparatus and method in which a rotating valve located in the patient circuit creates an oscillating pressure in the flow of gas to or from the patient.

2. Description of the Related Art

It is well known to provide ventilatory assistance to a patient suffering from a respiratory disorder using a pressure support system, such as a ventilator, to deliver a flow of breathing gas at a positive pressure to the patient's respiratory system. For patients with complete respiratory failure, a ventilator or other suitable pressure support device delivers a life supporting flow of breathing gas to the lungs. In less severe situations, the ventilator augments the patient's respiratory function to assist with the patient's work of breathing. In either of these situations, it is not uncommon for the patient using the ventilator to face gas diffusion problems, secretion clearance problems, or both.

Gas diffusion problems occur when the breathing gas supplied to the patient is not uniformly distributed through the lungs. When positive pressure ventilation is applied to some patients, the applied pressure and gas flow, instead of being uniformly distributed throughout the lungs, tends to extend the healthy part of the lungs farther than the not-as-healthy part of the lung, so that gas is distributed mainly to the health tissues in the lung. This difference between the extension in the healthy part and the not-as-healthy part of the lung can exacerbate the patient's lung condition, create a disproportionate gas exchange in the lungs, and may eventually damage the entire lung. Thus, it is desirable to minimize the pressure level applied to the patient's respiratory system while maximizing the diffusion of gas throughout the lungs in order to reduce the degree of difference between the extension in the healthy parts and the not-as-healthy parts of the lung.

Secretion clearance problems occur when there is a build up of secretions in the patient's respiratory system. In healthy patients, accumulated secretions are removed from the respiratory system by clearing the throat or coughing. In a ventilated patient, however, these secretion clearing movements cannot be performed easily, and, in some cases, cannot be performed at all. If the secretions are not removed in some other manner, they can accumulate in the patient, which increases the difficulty of properly ventilating the patient. A likely consequence is that even higher pressure levels must be provided to the patient in order to deliver the desired flow of breathing gas to the lungs. As noted above, it is preferable in many patients to keep the pressure levels of breathing gas delivered to a patient at a minimum.

A ventilation technique commonly known as "high frequency ventilation" is one method that addresses the gas diffusion and secretion clearance problems. According to this technique, the pressure of the gas flow delivered to the patient oscillates between two levels at a relatively rapid rate. Several mechanisms are known for introducing the pressure fluctuations in the gas flow. One common mechanism is to provide a flexible diaphragm in fluid communication with the gas flow in the patient circuit. For purposes of this disclosure, the patient circuit includes all components of a ventilation system that delivers the flow of breathing gas from the gas source, such as a pressure generator, to the patient. Vibrating the diaphragm generates pressure oscillations in the flow of gas in the patient circuit. Another mechanism for generating the pressure fluctuations in the gas flow is to introduce a series of small bursts of breathing gas into the primary gas flow.

While these ventilation techniques are believed to be effective in creating pressure oscillations in the primary flow of gas, they are disadvantageous in that they do not allow the pressure delivered to the patient to be a negative pressure during the oscillation cycle. In addition, it is difficult to control the oscillation magnitude and frequency with a high degree of precision and controllability while at the same time minimizing the complexity of the pressure oscillation generating mechanisms. Also, the above-described pressure oscillation techniques can only provide a somewhat limited range of magnitudes for the pressure variations in each oscillation cycle. For ventilation devices that use a flexible diaphragm to create the pressure oscillations, this limited range of magnitude in the pressure variation is due to the fact that a diaphragm displaces a finite amount of gas. For devices that use bursts of gas to create the pressure oscillations, this limited range of magnitude in the pressure variation is due to the fact that the magnitude of the gas pulses introduced into the primary flow must be limited so as to avoid introducing too much gas into the patient circuit. In addition, the gas pulses have a limited affect on the primary gas flow.

Secretion clearance can also be a problem in patients that are not using a ventilator. For example, a patient with a weakened respiratory system may not be physically able to perform a secretion clearing movement with sufficient strength or force to remove or loosen the secretions. For these patients, devices exist that create an abrupt pressure increase in the patient's airway to assist in dislodging or removing secretions. An example of such a device is a hand-held flutter valve, which uses a ball valve to create the pressure oscillations in the patient's airway. When the patient breathes into the flutter valve, the force of the patient's exhalation moves a ball off of a valve seat to open the valve. Gravity immediately urges the ball valve back onto the seat to obstruct the patient's expiratory flow until that the pressure is built up enough again to urge the ball off of the seat. This process repeats as the patient exhales until the patient's expiratory pressure is not great enough to move the ball off of the seat. A series of the pressure spikes occur in the patient's airway as a result of the temporary flow interruption caused by the closing and opening of the ball valve to facilitate loosening and removal of the patient's airway secretions.

There are disadvantages associated with the flutter valve secretion clearance device. For example, proper seating of the ball on the valve seat is only possible if the device is held in its upright position. Therefore, the device is very position sensitive. In addition, because the patient's own expiratory force is used to move the ball to the open position, the flutter valve cannot be used by patients with very weak respiratory systems who have very low expiratory flow.

Another device that is typically used by a patient who is not using a ventilator, and that provides pressure oscillations in which the pressure supplied to the patient can be made negative during a portion of the oscillation cycle, is the Emerson Cough-a-Lator produced by Emerson, Inc. This devices includes a mechanism that physically moves a portion of the patient circuit in a windshield wiper fashion between a position where the positive pressure output from a blower is coupled to the patient and position where the negative pressure at the input of the blower is coupled to the patient.

There is a significant disadvantage in the above-described pressure oscillation technique. Namely, the frequency of oscillation is limited to a relatively low level due to the fact that the device physically moves a portion of the patient circuit in a windshield wiper fashion. It is simply not possible to provide an oscillation frequency greater than approximately 2 Hz using this system. In addition, this system does not allow a pressure oscillation waveform to be superimposed on a second pressure waveform.

SUMMARY OF THE INVENTION

Accordingly, it is an object of the present invention to provide a high frequency pressure oscillation device that overcomes the shortcomings of conventional pressure oscillation techniques. This object is achieved according to one embodiment of the present invention by providing a high frequency pressure oscillation device that includes a patient circuit that couples a source of breathing gas to an airway of a patient and a valve disposed in the patient circuit. The valve is configured and arranged in the patient circuit so as to communicate the source of breathing gas with the airway of the patient when the valve is in a first position within the patient circuit. In addition, the valve at least partially restricts communication of the source of breathing gas with the airway of the patient when in a second position within the patient circuit. A rotating drive assembly rotates the valve in a first direction such that the valve is alternatively disposed in the first position and in the second position. This abrupt restriction or blockage of the pathway from the patient to the source of breathing gas produces pressure spikes in the patient's airway that are conducive to clearing secretions from the airway.

It is yet another object of the present invention to provide a high frequency pressure oscillation device that is capable of delivering positive and negative pressures to the airway of a patient during an oscillation cycle. This object is achieved according to the principles of the present invention by providing a high frequency pressure oscillation device as described in the immediately preceding paragraph, except that the source of breathing gas is a blower having an inlet and outlet. When in the first position, the valve communicates the outlet of the blower with the airway of a patient and communicates the inlet of the blower to ambient atmosphere. When the valve is in the second position, the valve communicates the inlet of the blower with the patient's airway and communicates the outlet of the blower to ambient atmosphere. By connecting the blower to atmosphere and to the patient in this manner, the positive and negative pressures at the outlet and inlet of the blower are provided to the patient in an alternating fashion as the valve rotates within the patient circuit.

It is a further object of the present invention to provide a high frequency pressure oscillation device that is capable of superimposing a high frequency pressure oscillation signal on another pressure signal. This object is achieved according to the principles of the present invention by providing a high frequency pressure oscillation device as described in the immediately preceding paragraph where the source of breathing gas is a first blower having an inlet and outlet. In addition, the high frequency pressure oscillation device of this embodiment includes a second blower having an inlet communicating with ambient atmosphere and an outlet. When in the first position, the valve communicates the outlet of the first blower with an airway of a patient and communicates the inlet of the first blower with the outlet of the second blower. When in the second position, the valve communicates the inlet of the first blower with an airway of a patient and communicates the outlet of the first blower with the outlet of the second blower. By connecting the first blower and the second blower to one another and to the patient in this manner, the positive and negative pressures at the outlet and inlet of the first blower are superimposed on the output of the second blower, which operates in any of a variety of pressure support modes.

It is another object of the present invention to provide a high frequency pressure oscillation method that overcomes the shortcomings of conventional pressure oscillation techniques. This object is achieved according to one embodiment of the present invention by providing a method that includes: (1) providing a patient circuit that communicates a source of breathing gas with an airway of a patient, (2) communicating the source of breathing gas with an airway of a patient when a valve in the patient circuit is in a first position within the patient circuit, (3) at least partially restricting communication of the source of breathing gas with the airway of the patient when the valve is in a second position within the patient circuit, and (4) rotating the valve in a first direction such that the valve is alternatively disposed in the first position and in the second position within the patient circuit. As noted above, this abrupt restriction, or complete blockage, if desired, of the pathway from the patient to the source of breathing gas produces pressure spikes in the patient's airway, especially as the patient exhales into the patient circuit, which are conducive to clearing secretions from the airway.

It is yet another object of the present invention to provide a high frequency pressure oscillation method in which positive and negative pressures are delivered to the airway of a patient during the oscillation cycle. This object is achieved according to the principles of the present invention by providing a method as described in the immediately preceding paragraph, except that the source of breathing gas is a blower having an inlet and outlet. The communicating step includes communicating the outlet of the blower with an airway of a patient and communicating the inlet of the blower to ambient atmosphere responsive to the valve being in the first position. Instead of restricting the communication between the source of breathing gas and the patient when the valve is in the second position, the method includes communicating the inlet of the blower with an airway of a patient and communicating the outlet of the blower to ambient atmosphere when the valve is in the second position. By connecting the blower to atmosphere and to the patient in this manner, the positive and negative pressures at the outlet and inlet of the blower are provided to the patient in an alternating fashion as the valve rotates in the patient circuit.

It is still a further object of the present invention to provide a method of ventilation or pressure support in which a high frequency oscillating pressure signal is superimposed on another pressure signal. This object is achieved according to the principles of the present invention by providing a method as described in the immediately preceding paragraph where the source of breathing gas is a first blower having an inlet and outlet. In addition, the method according to this embodiment of the invention includes providing a second blower having an inlet communicating with ambient atmosphere and an outlet. The communicating step includes communicating the outlet of the first blower with an airway of a patient and communicating the inlet of the first blower to the outlet of the second blower when the valve is in the first position. Instead of restricting the communication between the source of breathing gas and the patient when the valve is in the second position, the method of this embodiment includes communicating the inlet of the first blower with an airway of a patient and communicating the outlet of the first blower to the outlet of the second blower when the valve is in the second position. As a result the pressure oscillations provided by the first blower are superimposed on the pressure signal output by the second blower.

These and other objects, features and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF THE PRESENTLY PREFERRED EMBODIMENTS OF THE INVENTION

Figure 1:
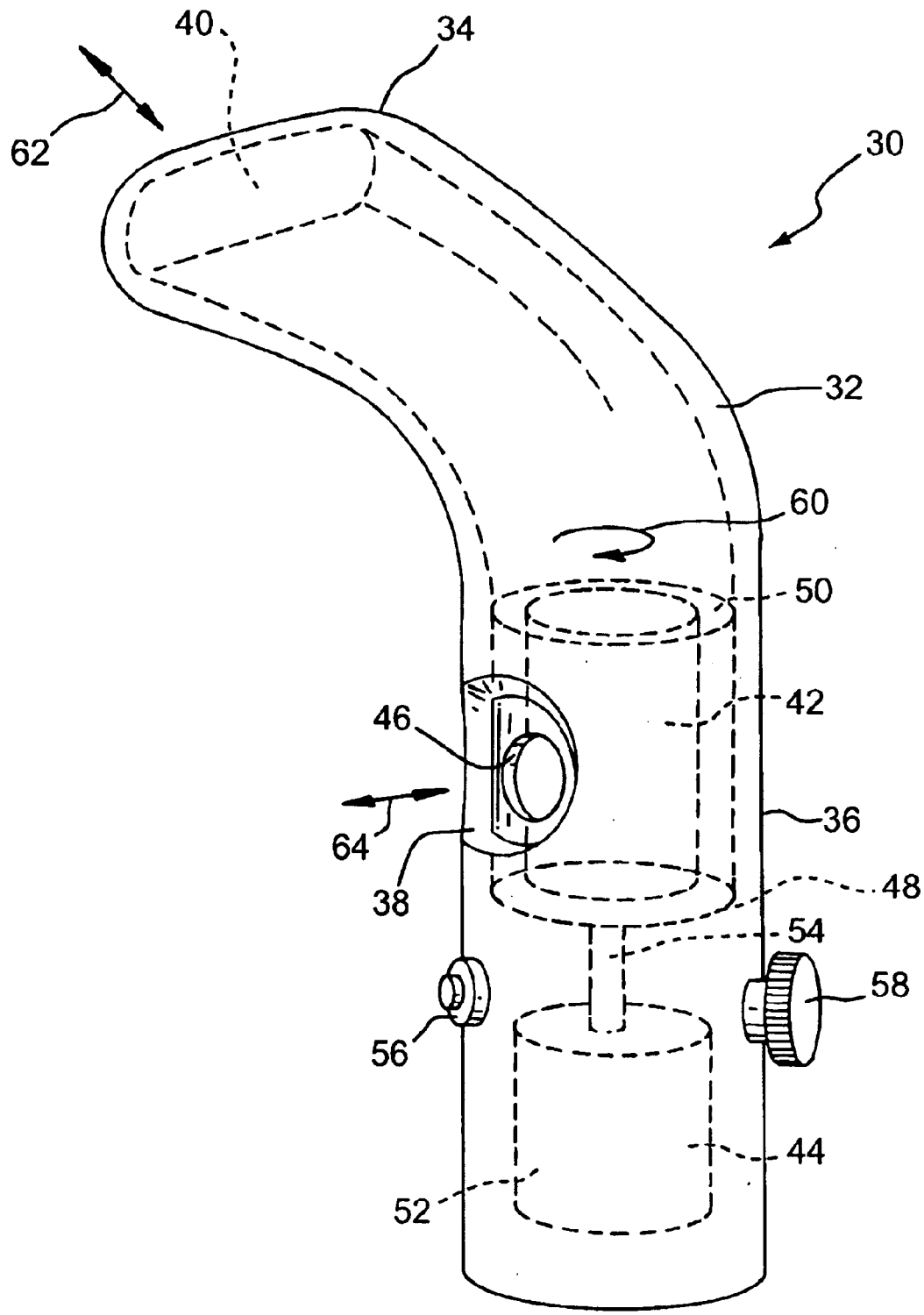
FIG. 1 is a perspective view of a high frequency pressure oscillation device according to a first embodiment of the present invention.

FIG. 1 illustrates a first embodiment of a high frequency pressure oscillation device 30 according to the principles of the present invention. Device 30 includes a patient circuit 32, which, in the illustrated exemplary embodiment, is a generally cylindrical conduit having a mouthpiece end 34 and a breathing gas source coupling end 36. A first port 38 is defined in end 36 so that breathing gas can enter the patient circuit and exhaled gas can vent from the patient circuit. Likewise, a second port 40 is defined in mouthpiece end 34 so that the patient can deliver and receive gas from the source of breathing gas through the patient circuit. In the illustrated embodiment, the source of breathing gas is ambient atmosphere. It is to be understood, however, that the source of breathing gas can be any supply of gas other than ambient atmosphere, such as oxygen or an oxygen mixture provided from a storage tank or a pressure generating device.

A valve 42 is disposed in patient circuit 32 at end 36 for selectively blocking and unblocking port 38. More specifically, valve 42 is disposed in patient circuit 32 so as to communicate the source of breathing gas with an airway of a patient when the valve is in a first position within the patient circuit, which corresponds to the position shown in FIG. 1. In addition, valve 42 substantially blocks communication of the source of breathing gas with the patient's airway when the valve is in a second position within the patient circuit. Valve 42 moves between the first and second positions by being rotated a first direction by a rotating drive assembly 44.

In the illustrated exemplary embodiment, valve 42 is a generally cylindrical member having a hollow central cavity that extends along its longitudinal axis. A third port 46 is defined in a side wall of the valve to communicate the exterior of the valve with the central cavity. A first end 48 of valve 42 is closed while a second end 50 has an opening defined therein that also communicates an exterior of the valve with the central cavity. Valve 42 provides an unobstructed gas flow pathway from the source of breathing gas to the patient's airway when third port 46 overlaps first port 38, i.e., when valve 42 is in the first position. When third port 46 does not overlap first port 38, i.e., when valve 42 is in the second position, the pathway from the source of breathing gas to the patient's airway is obstructed, so that substantially no gas flows from the patient to the breathing gas source or vice versa.

In the exemplary embodiment illustrated in FIG. 1, rotating drive assembly 44 includes an electric motor 52 that generates a torque for rotating valve 42 and a mechanical linkage 54 in the form of a drive shaft that couples the motor to valve 42 such that the rotational force output by the motor rotates the valve. A power supply (not shown), which can be any type of power supply, such as batteries or an AC source, provides energy to motor 52 when the device is activated by an on/off button 56. Preferably, motor 52 is a variable speed motor so that the frequency at which the flow path from the patient to the gas source is interrupted can be controlled by means of a speed control knob 58 or any other type of input device.

To use high frequency pressure oscillation device 30, the user energizes motor 52 by actuating on/off button 56. Motor 52 rotates valve 42 in one direction, as indicated, for example, by arrow 60, so that valve 42 is alternatively placed in the first position, in which first port 38 and third port 46 overlap, and the second position, in which first port 38 and third port 46 do not overlap. As noted above, this rotational movement of valve 42 alternatively communicates the source of breathing gas with the patient's airway and blocks such communication. It should be understood that while the direction of rotation is shown in FIG. 1 as being clockwise, the present invention also contemplates rotating the valve counterclockwise. In this embodiment, the actual direction of rotation is not important so long as the valve continues to be rotated in that direction.

The user breathes into mouthpiece end 34 so that a flow of gas is delivered to or received from the interior of patient circuit 32, as indicated by arrow 62, when valve 42 is in the first position. Gas is supplied to the interior of patient circuit 32 via ports 38 and 46 for consumption by the patient during inhalation or vented from the patient circuit during exhalation via the same port, as indicated by arrow 64, when valve 42 is in the first position. Because the free flow of gas between the patient and the gas source is periodically interrupted by valve 42 being in the second position, as the patient breathes into mouthpiece end 34, a series of the pressure spikes occur in the patient's airway as a result of the temporary flow interruption caused by the closing of first port 38. These pressure spikes facilitate loosening and removal of the patient's airway secretions. A similar result occurs as the patient inhales through mouthpiece end 34, except that instead of abrupt increases in pressure being created, abrupt decreases of pressure are generated in the patient's airway.

Although the embodiment of the present invention described above and shown in FIG. 1 interrupts the free flow of gas between the patient and the gas source during both the inspiratory and expiratory phases of the patient's breathing cycle, it is to be understood that the present invention contemplates interrupting the free flow of gas between the patient and the gas source only during one of these phases of the breathing cycle. For example, in one embodiment of the present invention, at all times during the inspiratory phase, the path between the patient and the gas source remain unobstructed and, during the inspiratory phase, the path between the patient and the gas source is at least partially unobstructed by the rotary valve. Of course, an appropriate one-way valve should be provided to ensure that gas flows freely to the patient during the inspiratory phase, i.e., does not flow through the rotating valve, and flows through the rotating valve during the expiratory phase. Alternatively, the rotating valve can be operated such that during the inspiratory phase, the ports in the rotary valve and the ports in the patient circuit overlap, thereby providing a substantially unobstructed path between the patient and the gas source, and during the expiratory phase the rotary valve rotates to at least partially obstruct this free flow of gas.

In the above-described embodiment, valve 42 substantially blocks the pathway from the source of breathing gas to the patient's airway when in the second position to create the desired pressure spikes. It is to be understood, however, that the present invention contemplates configuring the valve so that in the second position, the valve does not completely block this pathway; rather it provides an increase in the restriction to flow through the path. This abrupt increase in the restriction to flow between the patient's airway and the source of breathing gas, even though not a complete blockage, will also create pressure spikes that are sufficient to assist in secretion clearance.

It can be appreciated that a wide variety of configurations can be provided for patient circuit 32. For example, mouthpiece end 34 can be circular or oval, rather than the generally rectangular shape illustrated. In addition, the present invention contemplates providing a removeable mouthpiece that can be selectively detached from mouthpiece end 34 of patient circuit 32. It is to be further understood that more sophisticated control over the operation of the motor can be incorporated into the device. For example, the motor can be controlled so that its speed varies over the course of a treatment session. It should be noted that the specific components for controlling the motor and the interconnection of the input devices, i.e., on/off button 56 and speed control knob 58, are not illustrated in FIG. 1 for the sake of simplicity. It is believed that these components and interconnections would be well known to those skilled in the art.

Figure 2:
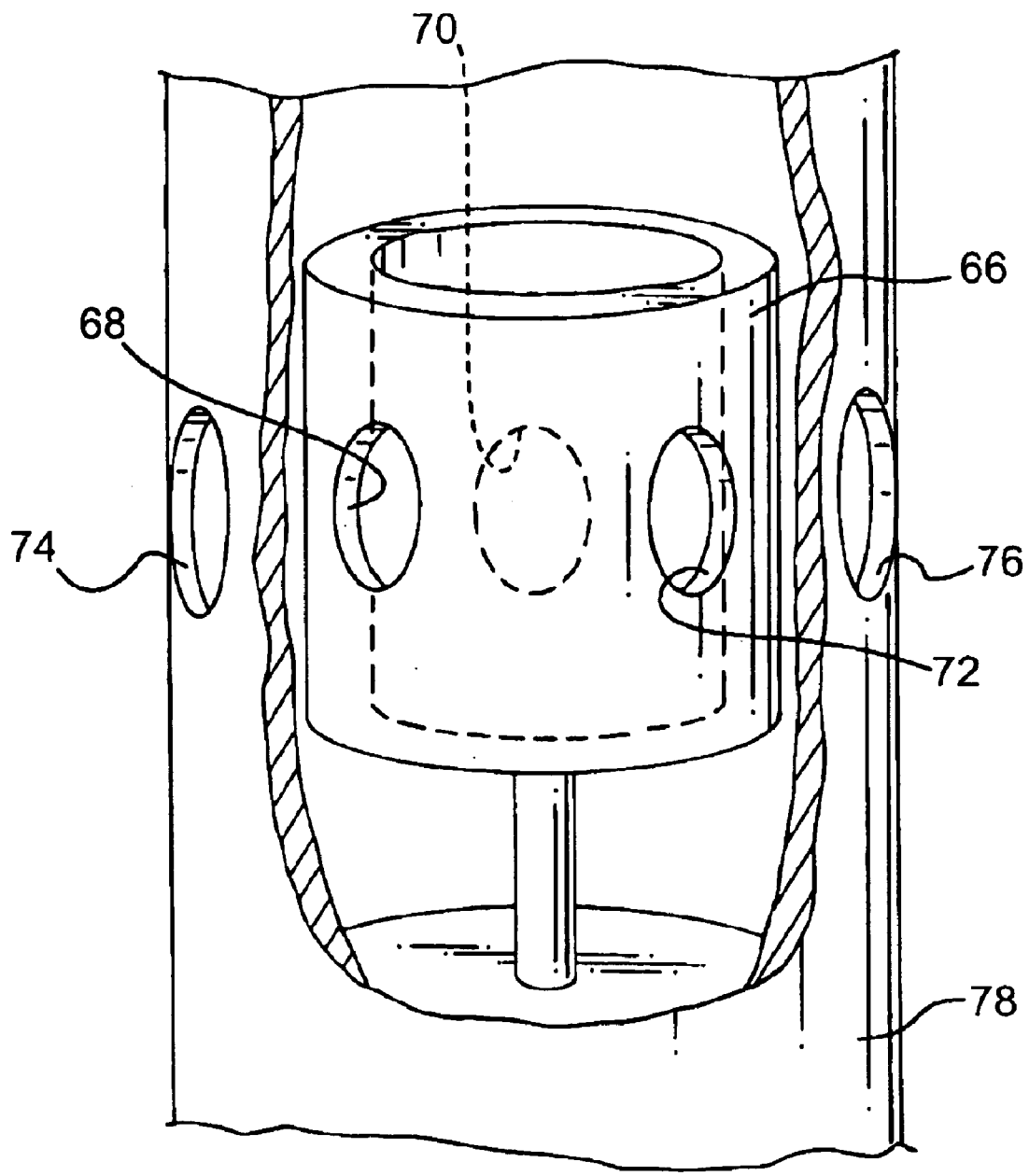
FIG. 2 is a perspective view illustrating a second embodiment of the rotary valve used in the high frequency pressure oscillation device of the present invention.

While FIG. 1 shows only one port in patient circuit 32 and valve 42, the present invention contemplates that more than one port can be provided in either or both of these components of device 32. For example, FIG. 2 illustrates a second exemplary embodiment of a rotary valve 66 that can be used in the high frequency pressure oscillation device of the present invention. In this embodiment, valve 66 includes a plurality of ports 68, 70, and 72 defined in the side wall of the valve, with all of the ports being aligned in generally the same circumferential location on the valve. In addition, FIG. 2 illustrates a plurality of ports 74 and 76 defined in patient circuit 78, with all of these ports also aligned in generally the same circumferential location on the patient circuit. It is to be understood, that multiple ports need not be provided in both the patient circuit and the rotary valve, as shown. On the contrary, the present invention contemplates providing multiple ports in only one of these components.

Those skilled in the art will appreciate that the number of ports, the shape or geometry of the ports, the location of the ports, and the size of the ports can be varied so that a wide variety of pressure signals or waveforms can be generated by the high frequency pressure oscillation device of the present invention. For example, the ports need not be circular, as shown, but can be rectangular, square, triangular, parabolic or any other shape, to provide different pressure curves to the patient, so long as the cooperation of the ports in the valve and ports in the patient circuit serve to obstruct the free flow of gas between the patient and ambient atmosphere, either completely or partially, so that pressure oscillations are generated in the patient's airway. In addition, the ports in the rotating valve or the patient circuit need not be evenly spaced apart from one another along the circumference of the rotating valve or the patient circuit, need not have the same size, and need not be centered in the same circumferential location about the valve or patient circuit as shown in FIG. 2. For example, the ports may be slight offset from one another to provide varying amounts of flow when at least a portion of a port in the rotating valve overlaps at least a portion of the port in the patient circuit.

It should be noted that valve 66 and patient circuit 78 are shown in FIG. 2 as being spaced apart from one another so that the ports in each can be clearly illustrated. Those skilled in the art understand that the functional high frequency pressure oscillation device should have a relatively small tolerance between these two components if a complete blockage of the flow of gas between the patient to the gas source is desired. If only a partial restriction of the flow of gas between the patient and the breathing gas source is desired, a clearance can be provided between the valve and the patient circuit so that even when the valve is in the second position, where the port of ports in the valve do not overlap the port or ports in the patient circuit, some gas will flow between the patient and the gas source around the exterior of the valve. FIG. 2 is believed to provide a clear illustration of the valve, including the opening defined in one of the axial surfaces of the valve that provides access to the central cavity defined in the valve. It should be noted that valve 66 in FIG. 2 is substantially the same as valve 42 in FIG. 1, except for the number of ports defined in the side walls of the valve.

Figure 3:
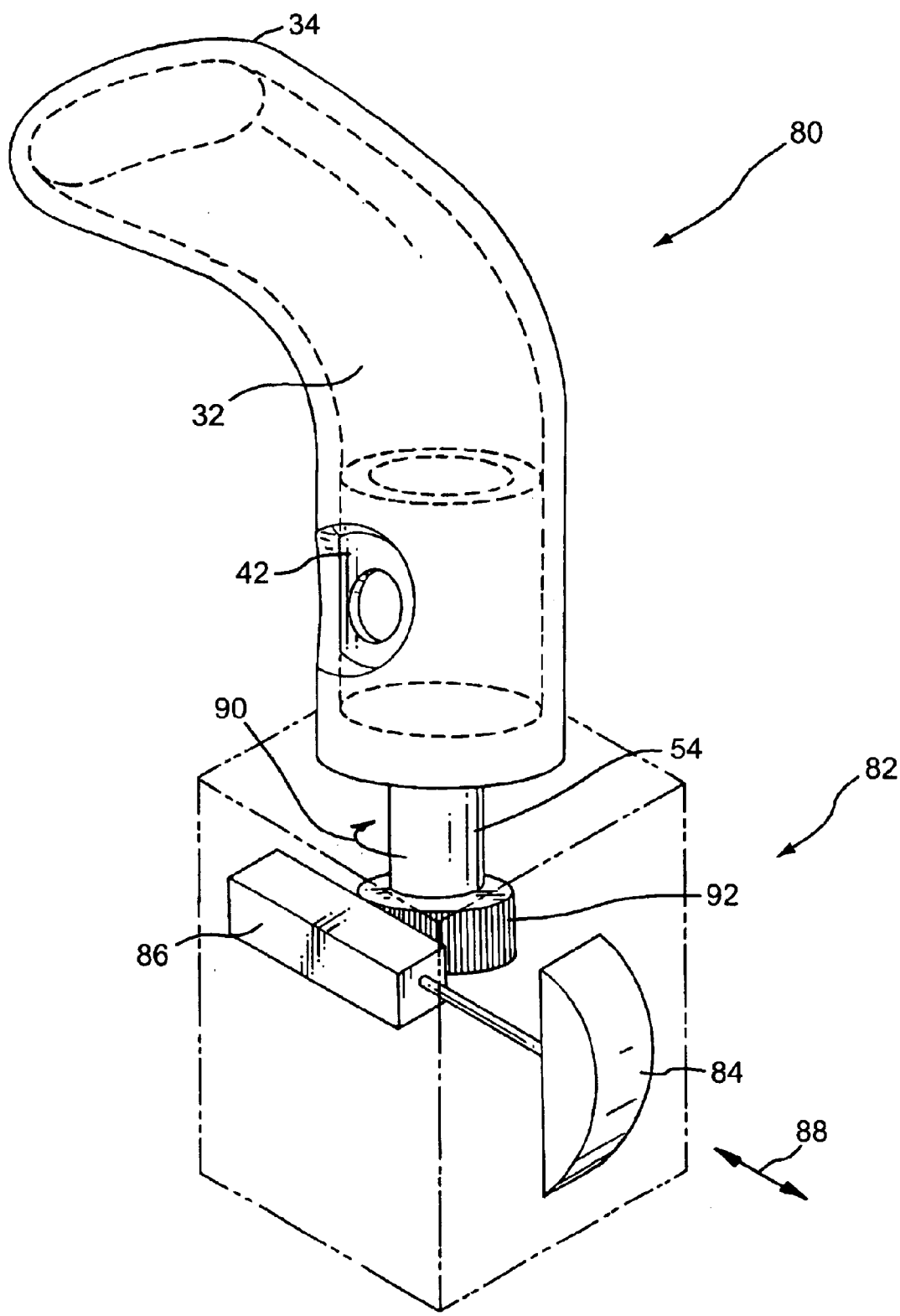
FIG. 3 is a perspective view of a high frequency pressure oscillation device according to a third embodiment of the present invention.
Figure 4:
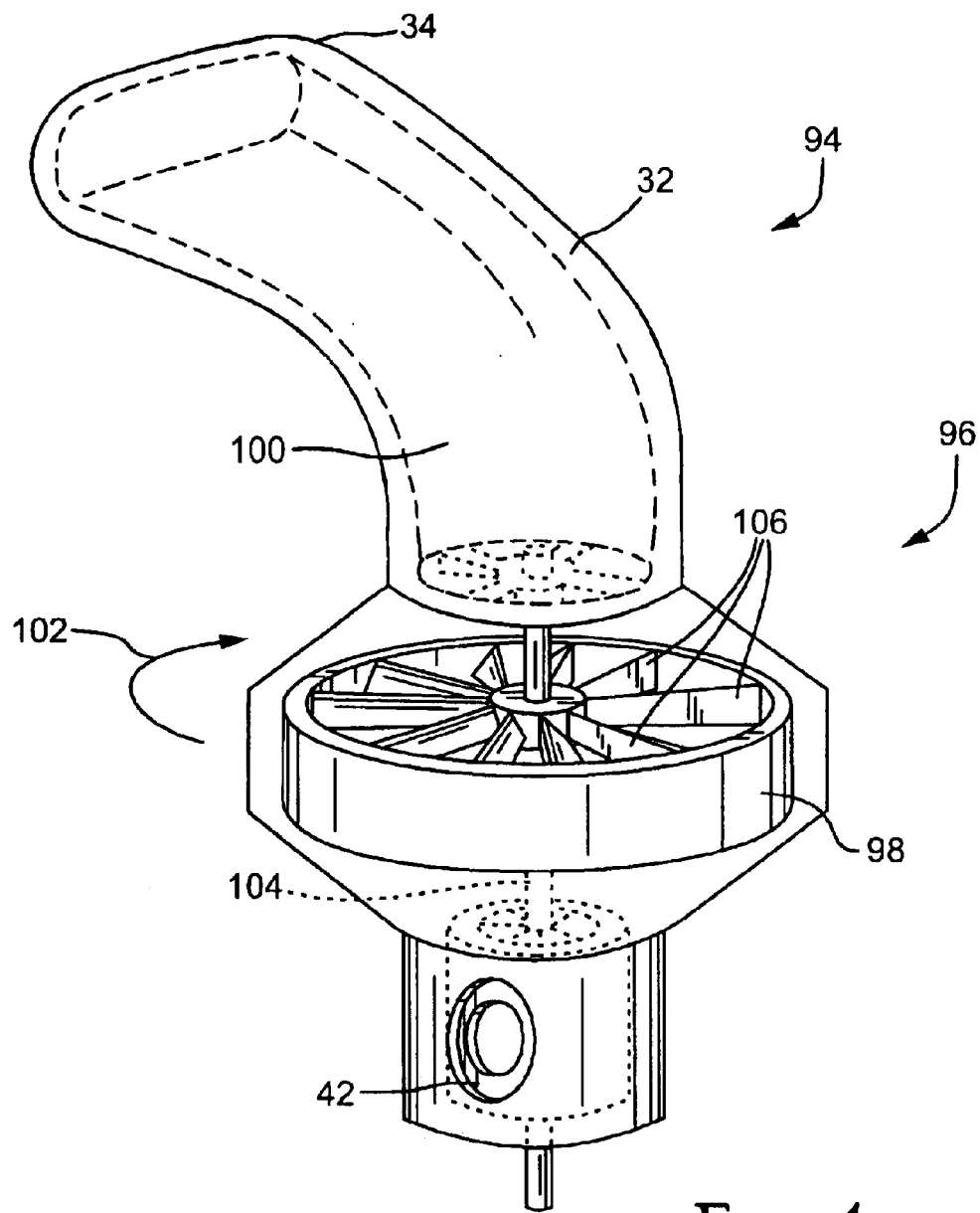
FIG. 4 is a perspective view of a high frequency pressure oscillation device according to a fourth embodiment of the present invention.

While FIG. 1 illustrates valve 42 as being rotated by an electric motor, the present invention contemplates other techniques for imparting a rotational force on the valve to cause it so spin in one direction. Two alternative techniques for rotating the valve, other than using a motor, are shown in FIGS. 3 and 4. High frequency pressure oscillation device 80 in FIG. 3 includes a manually operated system, generally indicated at 82, for rotating valve 42. This system includes a trigger 84 that is depressed by the user and a linkage 86 that moves laterally, as indicated by arrow 88, as a result of the trigger being depressed. Lateral movement of linkage 86 is translated into a rotational force, as indicated by arrow 90, by a gear 92 that engages linkage 86 as trigger 84 is depressed. This rotational force is translated to valve 42 via drive shaft 54. Preferably, a biasing mechanism (not shown) is provided in conjunction with linkage 86 to return the linkage and trigger 84 to their unactuated positions without affecting the rotation of shaft 54 so that the patient can repeatedly actuate trigger 84 to maintain the rotational movement of valve 42 while the patient breathes through patient circuit 32.

Figure 5:
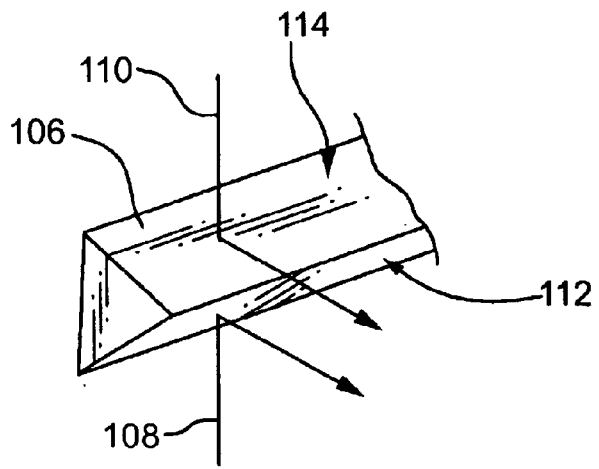
FIG. 5 is a perspective view of a blade or vane used in the rotary turbine illustrated in FIG. 4.

High frequency pressure oscillation device 94 in FIG. 4 includes a flow actuated turbine system, generally indicated at 96, for rotating valve 42. This system includes a turbine 98 disposed in patient circuit 100 such that a gas flow generated by a user induces rotation of the turbine. The rotational force generated by the turbine, as indicated by arrow 102, is imparted to valve 42 via drive shaft 104. In the illustrated exemplary embodiment, turbine 98 includes a plurality of radial blades 106 emanating from a central hub coupled to drive shaft 104. As shown in detail in FIG. 5, each blade is shaped so that flow through the turbine in either direction, i.e., inspiratory flow toward the patient, as indicated by arrow 108, or expiratory flow from the patient, as indicated by arrow 110, causes the turbine to rotate. For example, each blade 106 includes a first angled surface 112 and a second angled surface 114 that are situated such that when flow 108 to the patient or flow 110 from the patient impact on the surface, the force of the flow is translated into a sideways force that moves the blade, and, thus, moves the turbine.

As noted above, the present invention contemplates that the high frequency pressure oscillation device can include one or more ports in the valve or patient circuit. The more ports in either of these components, the higher the frequency of pressure oscillations in the patient's airway, assuming the rotational speed remains constant. Of course, as the speed of rotation increases, the frequency of the pressure oscillations also increases.

Figure 6:
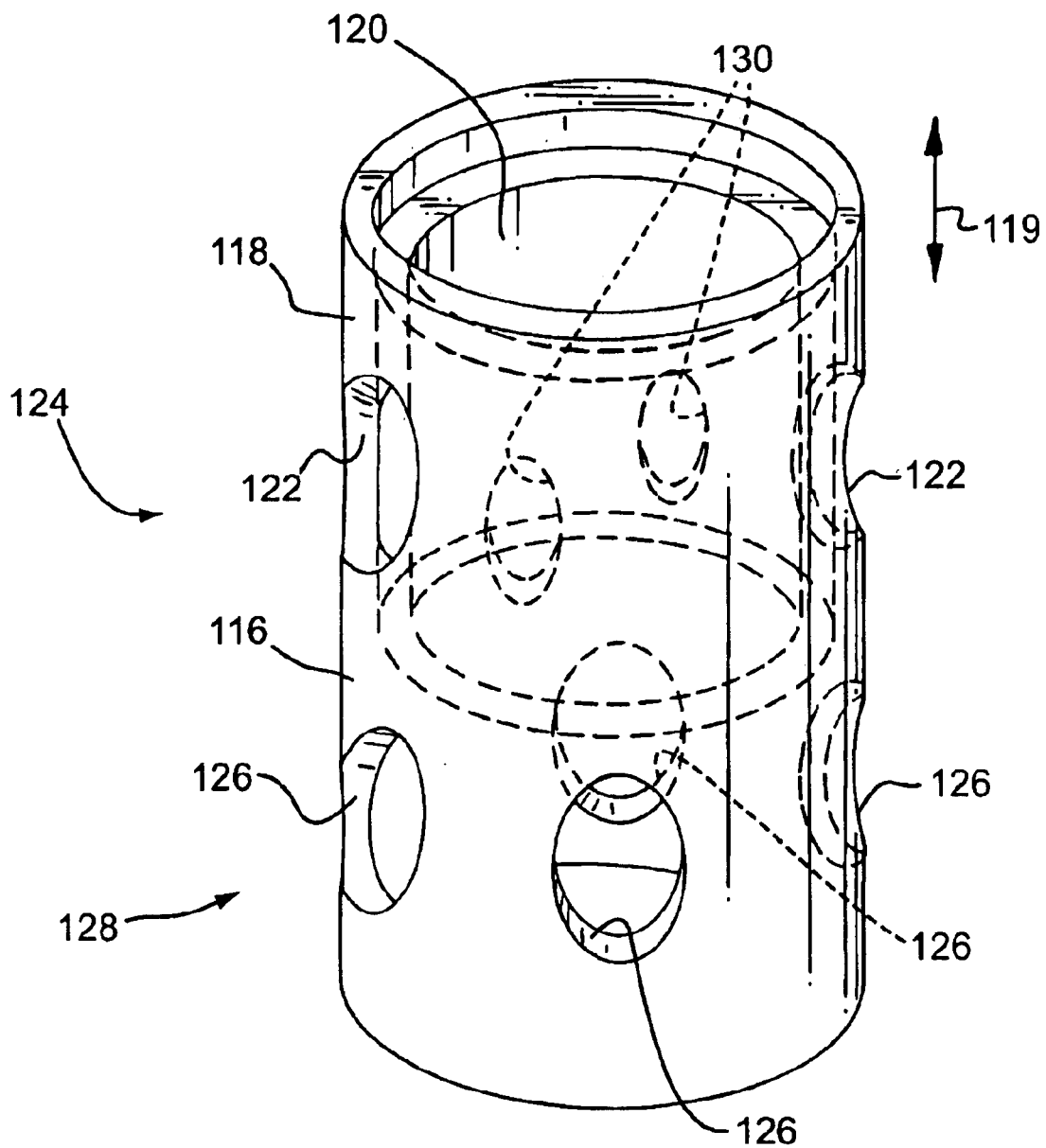
FIG. 6 is a perspective view illustrating a portion of a fifth embodiment of a high frequency pressure oscillation device of the present invention.

In the above embodiments, the ranges of frequencies of the pressure oscillations is limited by the range by which the speed of the motor can be varied. In addition, if the motor is a constant speed motor, the frequency of the pressure oscillations is also constant. FIG. 6, however, illustrates a further embodiment of a high frequency pressure oscillation device according to the principles of the present invention in which the frequency of the pressure oscillations can be varied independent of the motor speed. This is accomplished by providing the ability to change the number of ports in the patient circuit that align with the port of ports in the valve. It should be noted that FIG. 6 only illustrates a portion of the patient circuit.

As shown in FIG. 6, patient circuit 116 includes a conduit having a slideable portion 118 that moves axially relative to valve 120, as indicated by arrow 119. Slideable portion 118 includes a first number of ports 122 defined therein at a first circumferential location, generally indicated at 124, and a second number of ports 126 defined therein at a second circumferential location, generally indicated at 128. In the illustrated exemplary embodiment, two ports are provided at first circumferential location 124 and four ports are provided at second circumferential location 128. Ports 122 and 126 in the first and second circumferential locations 124 and 128, respectively, are capable of communicating an interior of patient circuit 116 to the breathing gas source when not blocked by valve 120.

The slideable portion is moveable in an axial direction relative to valve 120 so that in a first position, the first number of ports 122 at first circumferential location 124 are selectively blocked and unblocked by rotation of valve 120, while the second number of ports 126 at second circumferential location 128 remain blocked at all times during rotation of valve 120. FIG. 6 shows slideable portion 118 in this first position. When in a second position (not shown), the second number of ports 126 at the second circumferential location 128 are selectively blocked and unblocked by rotation of valve 120 and the first number of ports 122 at first circumferential location 124 are blocked at all times during rotation of valve 120. By selecting which set of ports are to be selectively unblocked by moving slideable portion 118 so that the desired set of ports is aligned with the ports in valve 120, the device of FIG. 6 allows the user to choose or adjust the frequency of the pressure oscillations.

Valve 120 in FIG. 6 includes two ports 130 for selectively unblocking ports 122 or 126 it rotates within patient circuit 116. It is to be understood, however, that the number, shape and size of the port or ports in valve 120 can be different from that shown. Similarly, the number, shape and size of the ports at the first and second circumferential locations in the patient circuit can also be different from that shown. In addition, further sets of ports at other circumferential locations can be provided in the patient circuit so that additional variations in the frequency of the pressure oscillations are possible.

In the embodiments described above and shown in FIGS. 1–6, the pressure oscillations are created in the patient's airway by repeatedly obstructing, either completely or partially, the flow of gas to or from the patient. In the embodiments described below and shown in FIGS. 7–13, the pressure oscillations are generated by a blower, and not by interrupting the patient's own flow.

It is well known that in a centrifugal blower, the relationship between pressure and tip speed can be defined as follows:

$$\Delta P_{dh} = \frac{\rho(\omega d)^2}{8}, \quad (1)$$

where $\Delta P_{dh}$ is the deadhead blower pressure, $\rho$ is the air mass density, $\omega$ is the motor speed, and d is the fan diameter. This same basic relationship is applicable to other types of fans, not just centrifugal blowers.

The deadhead blower pressure $\Delta P_{dh}$ always exists regardless of which side of the fan has a high impedance path to atmosphere so long as the other side is referenced directly to atmosphere, i.e., there is an unobstructed path to atmosphere. In electrical terms, referencing one side of the fan directly to atmosphere can be thought of as a ground. For example, if the inlet of the fan is grounded, i.e., left open to atmosphere, and the outlet of the fan is blocked, the pressure at the fan inlet will be zero or atmospheric pressure, while the pressure at the fan outlet will be $\Delta P_{dh}$. On the other hand, if the outlet of the fan is grounded, i.e., left open to atmosphere, and the inlet of the fan is blocked, the pressure at the fan inlet will be $-\Delta P_{dh}$ and the pressure at the fan outlet will be zero or atmospheric pressure. The present invention makes use of the positive and negative pressures that exist at the outlet and inlet of a fan by configuring the patient circuit and providing a valving system that allows these positive and negative pressures to be generated and applied to a patient.

Figure 7:
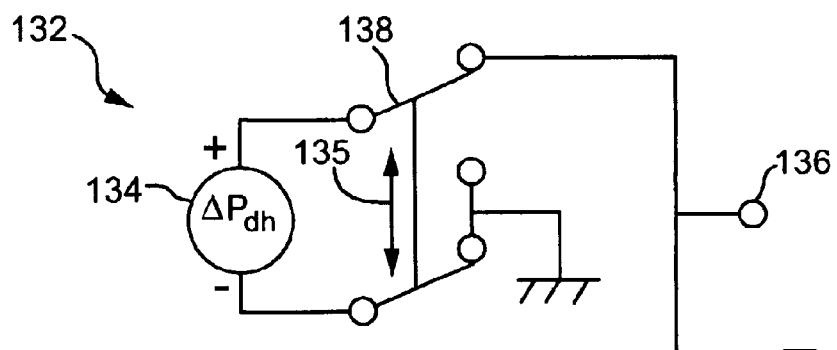
FIGS. 7, 8, and 9 are schematic diagrams of a high frequency pressure oscillation device according to sixth, seventh and eighth embodiments of the present invention, respectively.

FIG. 7 is a schematic diagram of a high frequency pressure oscillation device 132 according to the principles of the present invention in which the positive and negative pressures generated at the outlet and inlet of a blower are applied to the patient. More specifically, the positive and negative pressures are provided to the patient by alternatively connecting one side of a fan or blower 134 to a patient via a patient circuit 136, which essentially blocks that port of the fan, while connecting the other side of the fan to atmosphere, i.e., ground. This arrangement is then reversed to provide the other pressure to the patient.

For example, as shown in FIG. 7, a valve assembly 138 connects the outlet of fan 134 to the patient while connecting the inlet of fan 134 to atmosphere, which, as noted above, is shown as a ground. This configuration provides a positive pressure $\Delta P_{dh}$ to the patient. Then, this configuration is reversed by causing valve assembly 138 to connect the outlet of fan 134 to atmosphere, i.e., ground, while connecting the inlet of fan 134 to the patient. Arrow 135 in FIG. 7 indicates how valve assembly 138 would move to provide the connections. This latter configuration provides a negative pressure $-\Delta P_{dh}$ to the patient. By repeatedly reversing these configurations using the valve assembly, the pressure support system provides a periodic or oscillating pressure to the patient with a mean level of atmospheric pressure (0 atm) and amplitudes of oscillation that have equal magnitudes in both the positive and negative directions and equal to $|\Delta P_{dh}|$. Details of valve assembly 138, which provides this capability of alternating the connections of the inlet and the outlet of the fan between atmosphere and the patient, are described below with respect to FIGS. 10–12.

Figure 8:
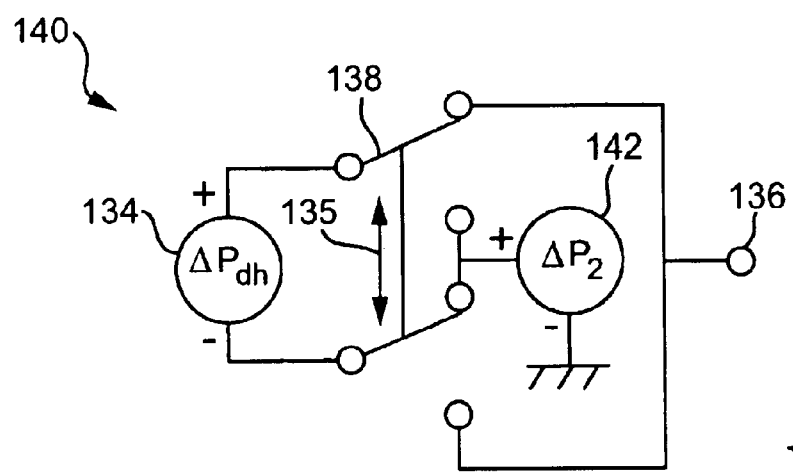

FIG. 8 illustrates a further embodiment of a high frequency pressure oscillation device 140 according to the principles of the present invention, which is a variation on the embodiment shown in FIG. 7. The device shown in FIG. 8 provides the ability to superimpose the oscillating pressure discussed above on a second pressure $\Delta P_2$, such as a continuous positive airway pressure (CPAP), bi-level pressure or any other type of pressure waveform. This is accomplished by providing a second fan or blower 142 that connects to the inlet or outlet of first blower 134 instead of atmosphere, as is the case with the device of FIG. 7. In essence, the ground in FIG. 7 is replaced with a second pressure support signal so that the oscillating pressures created by first fan 134 are superimposed on the output of second fan 142. In this configuration, the oscillation pressure $\Delta P_{dh}$ from fan 134 is boosted by the pressure $\Delta P_2$ from fan 142 so that the total pressure provided to the patient is $\Delta P_2 \pm \Delta P_{dh}$. It can be appreciated that if the magnitude of $\Delta P_{dh}$ is greater than $\Delta P_2$, the total pressure during at least a portion of the negative phase of the oscillation cycle will be less than atmospheric.

It should be emphasized that the magnitude and shape of the pressure signal $\Delta P_2$ output by fan 142 are arbitrary. Pressure signal $\Delta P_2$ can be a bi-level pressure waveform, as taught, for example, in to U.S. Pat. No. 5,148,802 to Sanders et al., U.S. Pat. No. 5,313,937 to Zdrojkowski et al., and U.S. Pat. No. 5,433,193 to Sanders et al. Pressure signal $\Delta P_2$ can also be a CPAP signal, a proportional assist ventilation (PAV) pressure, as taught, for example, in U.S. Pat. No. 5,107,830 to Younes, a proportional positive airway pressure (PPAP), as taught, for example, in U.S. Pat. Nos. 5,535,738 and 5,794,615 both to Estes, or even another oscillating pressure.

In the device schematically illustrated in FIG. 7, the oscillating pressure occurs about a mean of $P_{atm}$ or atmospheric pressure. Although this pressure can be offset using a second pressure source, as shown in FIG. 8 and described above with respect to this figure, is it not necessary to have an additional pressure source to implement a simple mean pressure or "DC" offset. This can be accomplished, for example, by providing valves 144 and 146, which are schematically illustrated in high frequency pressure oscillation device 148 of FIG. 9 as variable resistances coupled to ground, that are connected on either side of fan 134 to atmosphere.

Figure 9:
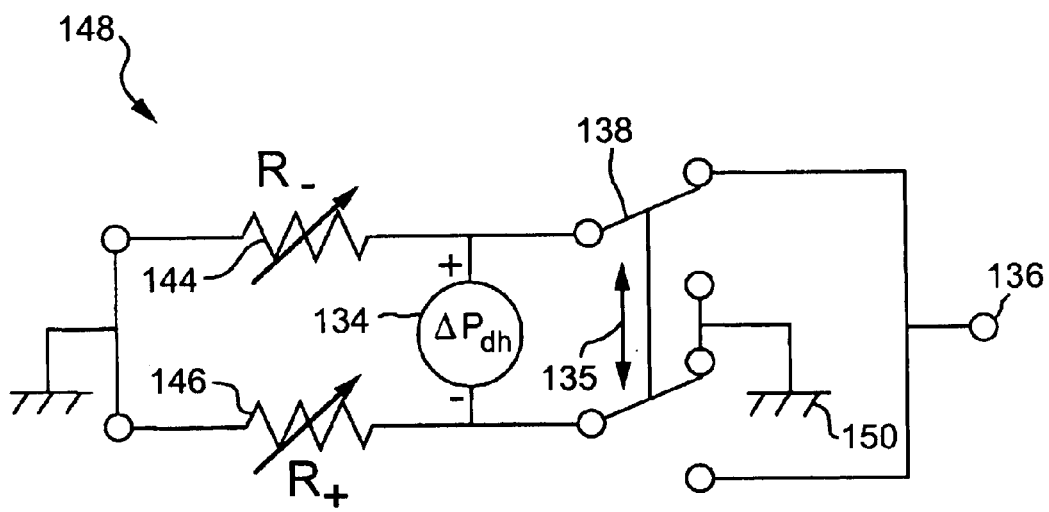

If $R_+$ and $R_-$ are blocked or configured to provide a very high impedance, the pressure support system will operate as described above with respect to FIG. 7. High frequency pressure oscillation device 148 of FIG. 9 does not include a second fan, such as fan 142 of FIG. 8. The present invention contemplates, however, providing a second fan in place of a connection to atmosphere, i.e., ground 150, as shown in FIG. 9. In which case, if $R_+$ and $R_-$ are blocked or configured to provide a very high impedance, the pressure support system will operate as described above with respect to FIG. 8.

As $R_-$ is opened to provide less of an impedance to atmosphere, the oscillation pressure signal seen at the patient pressure point is shifted or offset in the negative direction. Likewise, as $R_+$ is opened to provide less of an impedance to atmosphere, the oscillation pressure signal seen at the patient pressure point is shifted or offset in the positive direction. While FIG. 9 illustrates valves 144 and 146 connected to the outlet and inlet, respectively, of fan 134, it is to be understood that the present invention contemplates providing only one such valve depending on the desired control for the pressure signal to be achieved.

The details of one exemplary embodiment of high frequency pressure oscillation device 140 schematically shown in FIG. 8 are provided below with reference to FIG. 10, which is a perspective view of the elements in high frequency pressure oscillation device 140, and with reference to FIGS. 11 and 12, which are perspective and side sectional views, respectively, of a rotary valve 152 used as valve assembly 138 in the high frequency pressure oscillation device of FIG. 8. It can be appreciated that the details of valve assembly 138 shown in FIGS. 10–12 are equally applicable to the valve assemblies 138 of FIGS. 7 and 9.

Figure 10:
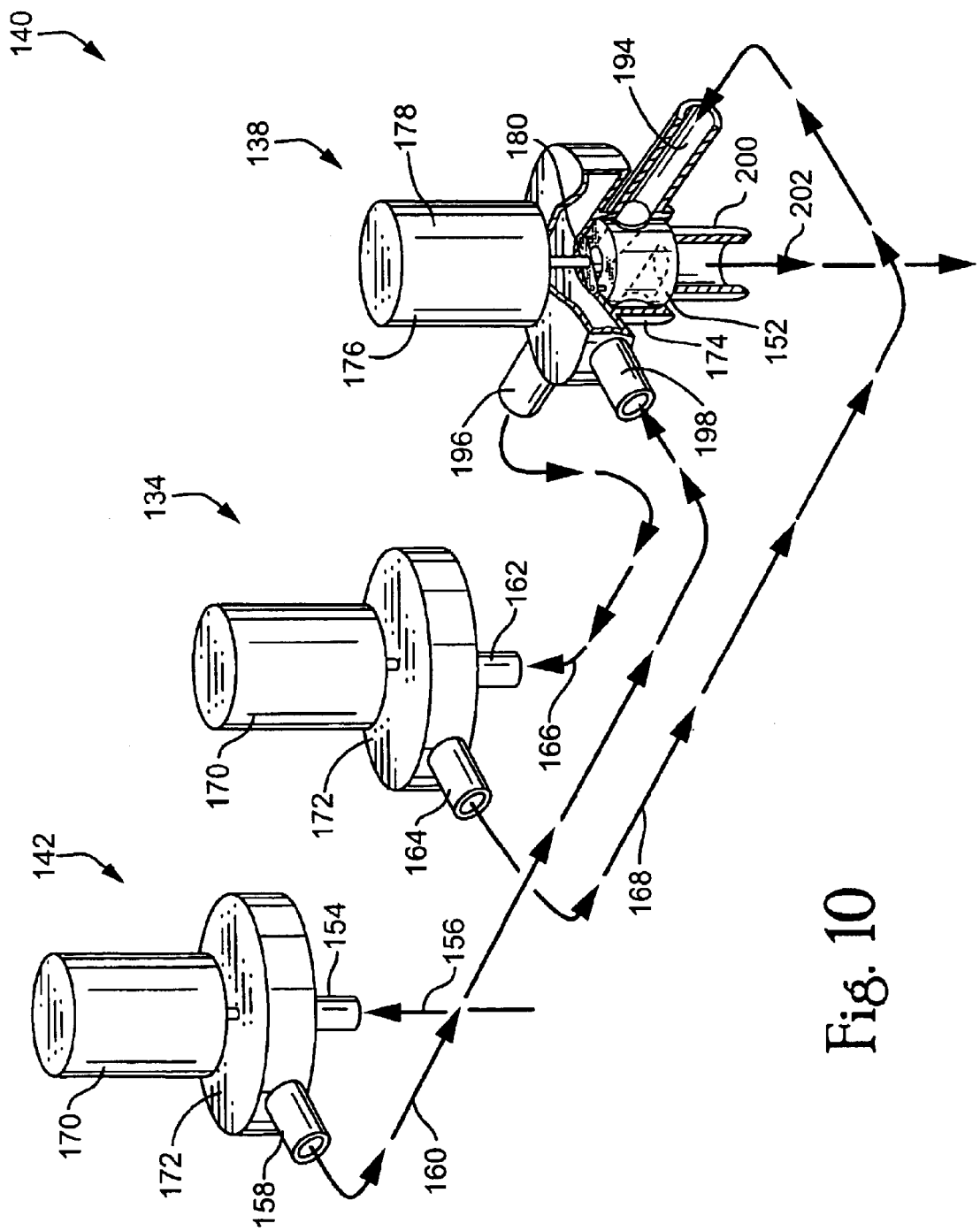
FIG. 10 is a perspective view of the elements in the high frequency pressure oscillation device of FIG. 8.

As shown in FIG. 10, an inlet 154 of second blower 142 receives breathing gas from a source of breathing gas, such as ambient atmosphere, as indicated by arrow 156. It should be noted that other sources of breathing gas, such as oxygen, helium, heliox, an oxygen mixture, or a breathing gas containing medicated aerosol, for example, can be used in conjunction with the second blower. An outlet 158 of second blower 142 is coupled to valving assembly 138, as indicated by arrows 160. Both inlet 162 and outlet 164 of first blower 134 are coupled to valving assembly 138, as indicated by arrows 166 and 168 respectively. In the illustrated exemplary embodiment, blowers 134 and 142 are each centrifugal blowers having a motor 170 that drives a turbine 172.

Valve assembly 138, which performs the pneumatic switching function shown in FIGS. 7–9, includes a generally cylindrical rotary valve member 152, a valve housing 174 in which cylindrical rotary valve member 152 is located, and a rotating drive assembly 176 coupled to valve member 152 to rotate the valve member in a first direction, i.e., clockwise or counter-clockwise, within valve housing 174. In the exemplary embodiment, rotating drive assembly 176 includes a rotary motor 178 that is coupled to valve member 152 via a mechanical linkage 180.

Figure 11:
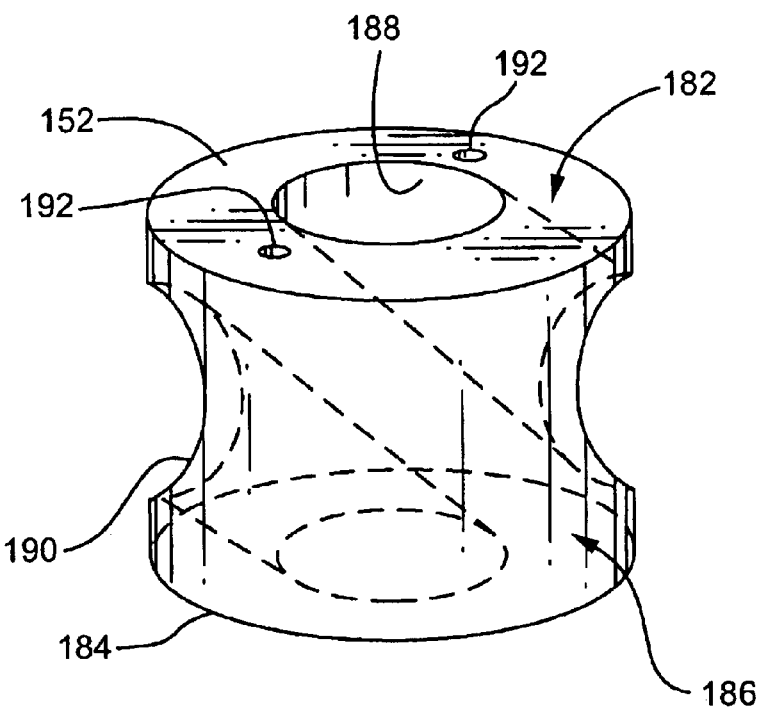
FIGS. 11 and 12 are perspective and side sectional views, respectively, of the rotary valve used in the high frequency pressure oscillation device of FIGS. 7–10.
Figure 12:
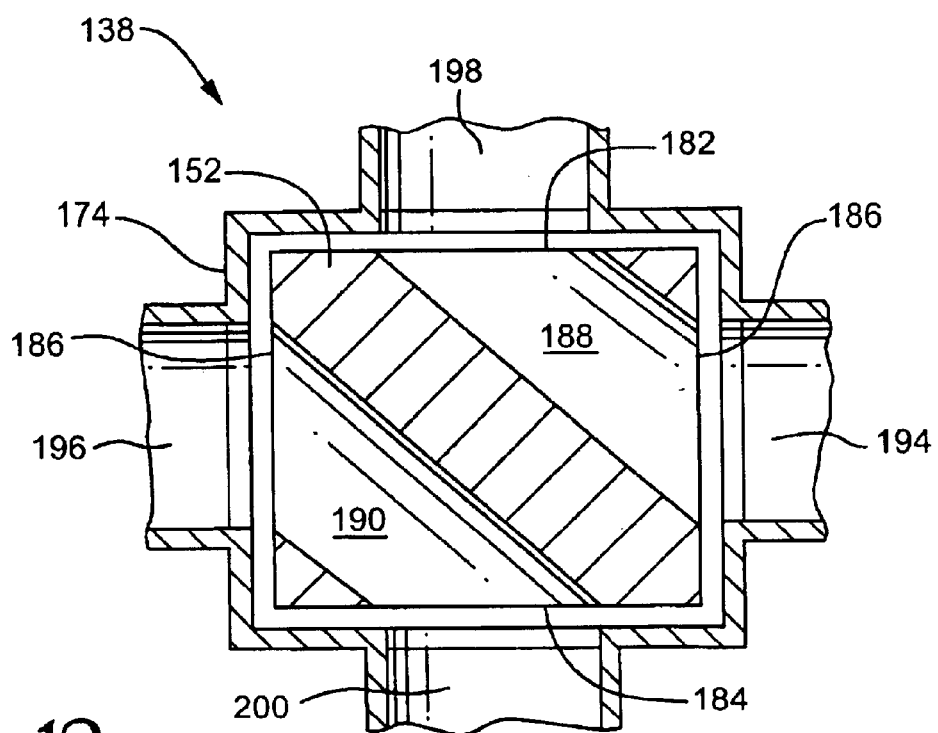

As shown in FIGS. 11 and 12, cylindrical rotary valve member 152 has a first axial surface 182, a second axial surface 184, and a side surface 186. A first hole 188 is defined in the valve member such that that the first hole extends from first axial surface 182 to a first portion of side surface 186. A second hole 190 is also defined in the valve member such that the second hold extends from second axial surface 184 to a second portion of side surface 186 of the valve member. Preferably, the first portion of the side surface of the cylindrical valve member associated with first hole 188 and the second portion of the side surface of the cylindrical member associated with second hole 190 are opposite one another so that valve member 152 remains balanced as it rotates. As shown in FIG. 11, in an exemplary embodiment, first axial surface 182 also includes a pair of mounting holes 192 for coupling the valve member to mechanical linkage 180.

Valve housing 174 includes a chamber defined therein that receives cylindrical rotary valve member 152 so that the valve member can rotate within the valve chamber. Although not shown, it can be appreciated that sealing elements, such as gaskets and o-rings, and rotation elements, such as bearings, can be provided to facilitate the rotational of valve 152 within the chamber. A first conduit 194 couples outlet 164 of first blower 134 to a first side of the valve chamber. A second conduit 196 couples inlet 162 of first blower 134 and a second end of the valve chamber. Preferably, the first side and the second side of the valve chamber to which the outlet and the inlet of the first blower are coupled, respectively, are located on opposite sides of valve housing 174. A third conduit 198 couples outlet 158 of second blower 142 with a first end of the valve chamber. In addition, a fourth conduit 200 couples a second end of the valve chamber to the airway of a patient, as indicated by arrows 202.

In operation, valve member 152 spins in one direction, clockwise or counterclockwise, within valve housing 174. The speed of rotation is controlled by rotating drive assembly 176. When in a first position (not shown), valve member 152 communicates first conduit 194 with fourth conduit 200 via second hole 190, so that outlet 164 of first blower 134 communicates with the airway of the patient. Also, when in the first position, valve member 152 simultaneously communicates second conduit 196 with third conduit 198 via first hole 188, so that inlet 162 of first blower 134 communicates with outlet 158 of second blower 142. As a result of this configuration, the pressure supplied to the patient when valve member 152 is in the first position corresponds to $\Delta P_2 + \Delta P_{dh}$.

It is to be understood, that if the second blower is eliminated so that the high frequency pressure oscillation device has the configuration shown in FIG. 7, the inlet of the first blower communicates with ambient atmosphere via the fluid connection between second conduit 196 and third conduit 198, because, in the configuration of FIG. 7, third conduit 198 communicates with ambient atmosphere, not with a second blower. In which case, the pressure supplied to the patient when valve member 152 is in the first position corresponds to $\Delta P_{dh}$.

When in a second position, which is shown in FIGS. 10 and 12, valve member 152 communicates second conduit 196 with fourth conduit 200 via second hole 190, so that inlet 162 of first blower 134 communicates with the airway of the patient. Also, when in the first position, valve member 152 simultaneously communicates first conduit 194 with third conduit 198 via first hole 188, so that outlet 164 of first blower 134 communicates with outlet 158 of second blower 142. As a result of this configuration, the pressure supplied to the patient when valve member 152 is in the first position corresponds to $\Delta P_2 - \Delta P_{dh}$.

If the second blower is eliminated so that the high frequency pressure oscillation device has the configuration shown in FIG. 7, the outlet of the first blower communicates with ambient atmosphere via the fluid connection between first conduit 194 and third conduit 198, because, in the configuration of FIG. 7, third conduit 198 communicates with ambient atmosphere, not with a second blower. In which case, the pressure supplied to the patient when valve member 152 is in the second position corresponds to $-\Delta P_{dh}$.

It can thus be appreciated that in the first position, the pressure supplied to the patient corresponds to $\Delta P_2 + \Delta P_{dh}$, and in the second position, the pressure supplied to the patient corresponds to $\Delta P_2 - \Delta P_{dh}$. If the second blower is eliminated, as is the case in the device of FIG. 7, the pressure supplied to the patient corresponds to $\Delta P_{dh}$, and in the second position, the pressure supplied to the patient corresponds to $-\Delta P_{dh}$. In addition, the high frequency pressure oscillation device rapidly transitions from the first position to the second position and vice versa at a rate set by the speed of motor 178 so that the patient is presented with a pressure signal having a rapidly varying oscillatory component. This pressure oscillation is superimposed on a second pressure signal, if a second blower is used, see FIG. 8, or is provided alone if no additional blower is used, see FIG. 7. The oscillation frequency that can be achieved using the rotary valve pneumatic switching technique of the present invention are as high as 100 Hz.

In the illustrated exemplary embodiments, first hole 188 and second hole 190 are generally circular channels defined in the valve member from one end surface to a first or second portion of the side surface of the valve member. It is to be understood, however, that the first and second holes can have other shapes, sizes, and configurations to provide various pressure signals or waveforms. For example, the size of the openings of the first and second holes in the side surface of the valve member can be increased, at least in the circumferential direction, to minimize the dead space on the side surface of the valve member between these openings, thereby providing a more rapid transition for the high and low (or negative) pressures during the pressure oscillation cycle.

Similarly, in the illustrated exemplary embodiments, first conduit 194 and second conduit 196 coupled to valve housing 174 are generally circular channels with generally circular openings defined in the inside wall within the valve housing. It is to be understood, however, that the first and second conduit, and, more particularly, the openings of the first and second conduits defined in the inside wall of the valve housing can have other shapes, sizes, and configurations to provide various pressure signals or waveforms.

Figure 14A:
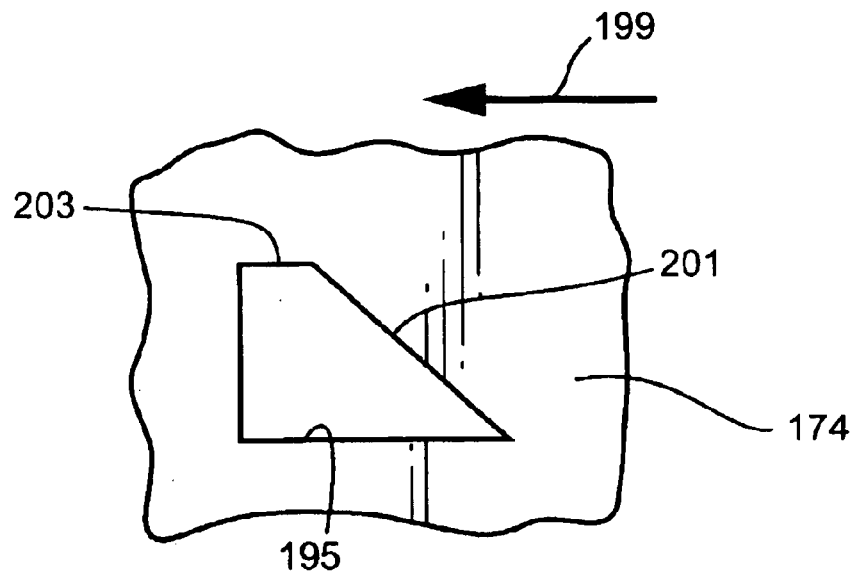
FIGS. 14A and 14B illustrate alternative configurations for openings in first and second conduits on an interior side wall of the valve assembly.
Figure 14B:
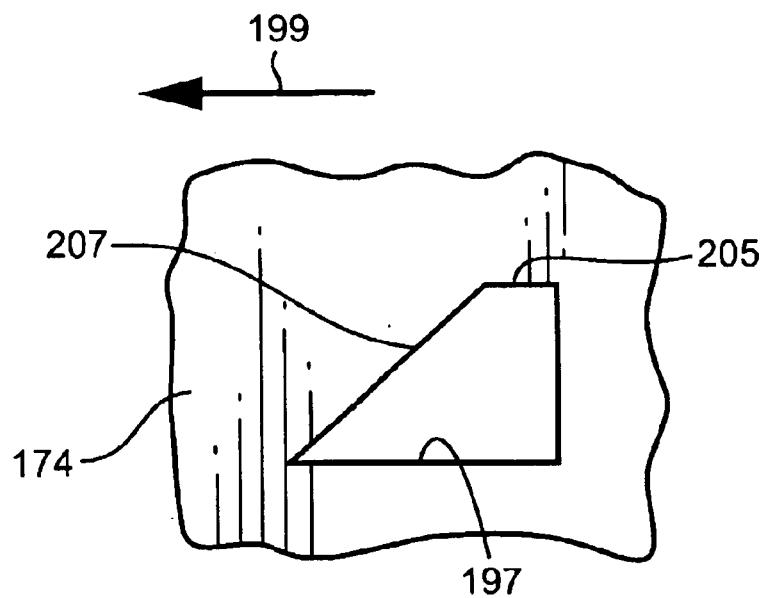

For example, the present invention contemplates shaping a first opening 195 associated with first conduit 194, which is coupled to outlet 158 of second blower 142, and shaping a second opening 197 of second conduit 196, which is coupled to inlet 162 of first blower 134, as shown in FIGS. 14A and 14B. The openings in the first and second holes in the side surface of the valve member can be as shown in FIGS. 10 and 11, or, more preferably, rectangular. Arrow 199 shows the direction of travel of the openings in the first and second holes in the side surface of the valve member over first and second openings 195 and 197. As shown in FIG. 14A, first opening 195 is configured such that the area of first opening 195 that overlaps the opening in the rotating valve gradually increases in an area 201 as the opening in the rotating valve passes over first opening 195, and a maximum overlap is provided at area 203. As a result, the pressure increase provided to the patient during a pressure oscillation cycle occurs gradually so that the patient's airway gradually fills with gas. On the other hand, as shown in FIG. 14B, second opening 197 is configured that the area of the opening overlapping the opening in the rotating valve is at a maximum in an area 205 as the opening in the rotating valve begins to pass over second opening 197, and gradually decreases in an area 207. As a result, the pressure decrease provided to the patient during a pressure oscillation cycle occurs very quickly so that the gas is rapidly evacuated from the patient's airway. In effect, this configuration fills the patient's airway relatively slowly and removes gas from patient's airway relatively rapidly during each pressure oscillation cycle as valve 152 rotates in housing 174, thereby maximizing the secretion clearance capabilities of the present high frequency pressure oscillation device.

In the exemplary embodiment shown in FIG. 10, three motors are used to operate the first blower, the second blower, and the rotating drive assembly that rotates valve member 152. The present invention contemplates an embodiment of a high frequency pressure oscillation device 204, as shown FIG. 13, that uses a single motor 206 to operate these three components. Motor 206 rotates a drive shaft 208 that is coupled to a first impeller 210, which functions as first blower 134 in the embodiments of FIGS. 7–12. Drive shaft 208 is also coupled to a second impeller 212, which functions as second blower 142 in the embodiments of FIGS. 8–12, and cylindrical rotary valve member 152. Of course, if the second blower is eliminated, as in the pressure support system of FIG. 7, second impeller 212 is eliminated so that motor 206 drives only impeller 210 and valve member 152.

Because it may be desirable that first impeller 210, second impeller 212, and cylindrical rotary valve member 152 not all operate at the same rotational speed, a first mechanical coupling 214 and a first clutch 216, such as an electromagnetic clutch, is provided between first impeller 210 and second impeller 212. In addition, a second mechanical coupling 218 and a second clutch 220, such as an electromagnetic clutch, is provided between motor 206 and valve member 152. Preferably, a control mechanism (not shown) is provided for actuating clutches 216 and 220.

Figure 13:
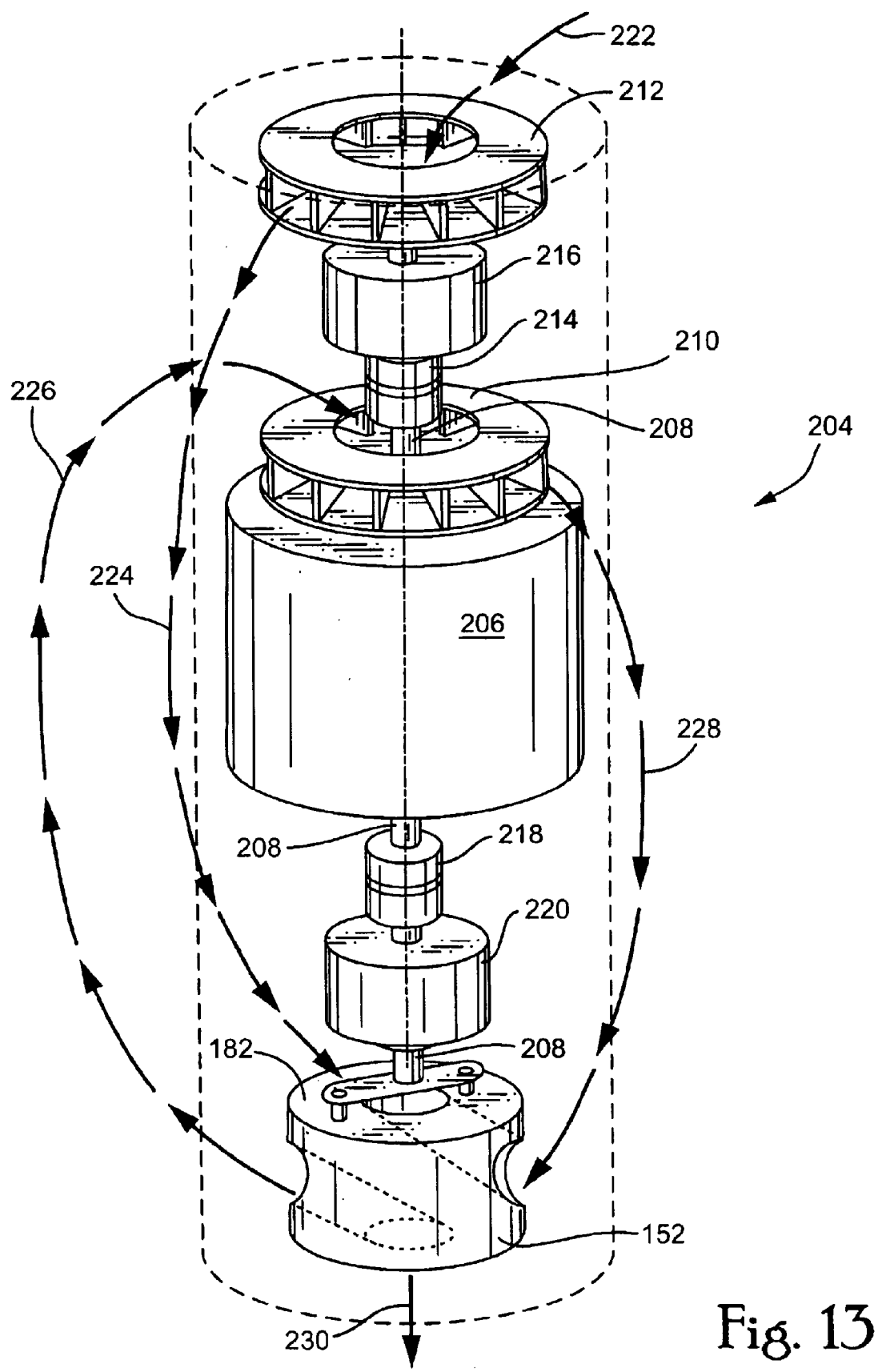
FIG. 13 is a perspective view of a high frequency pressure oscillation device according to a ninth embodiment of the present invention.

Although FIG. 13 does not show the conduits that couple the inlet and outlet of first impeller 210 and second impeller 212 to the other components of high frequency pressure oscillation device 204 for ease of illustration, it should be noted that the interconnections of these elements are the same as discussed above with respect to FIGS. 7–12. For example, the inlet of second impeller 212 communicates with ambient atmosphere, as indicated by arrow 222. The outlet of second impeller 212 communicates with the opening defined in axial surface 182 of valve member 152 corresponding to third conduit 198 in FIG. 12, as indicated by arrow 224, so that the outlet of the second impeller is alternatively coupled to the inlet and outlet of first impeller 210 as valve member 152 rotates between the first and second positions. The inlet and outlet of first impeller 210 communicate with either side of valve element 152, as indicated by arrows 226 and 228. Also, the patient circuit connects to the opening defined in second axial surface 184, as indicated by arrow 230, so that the outlet and the inlet of the first impeller are alternatively coupled to the patient circuit as valve member 152 rotates between the first and second positions.

Although the invention has been described in detail for the purpose of illustration based on what is currently considered to be the most practical and preferred embodiments, it is to be understood that such detail is solely for that purpose and that the invention is not limited to the disclosed embodiments, but on the contrary, is intended to cover modifications and equivalent arrangements that are within the spirit and scope of the appended claims.

What is claimed is:

1. A high frequency pressure oscillation device comprising:
   a patient circuit having a first end adapted to be coupled a source of breathing gas and a second end adapted to be coupled to an airway of a patient, wherein the patient circuit carries a flow of breathing gas between the source and the airway of such a patient;
   a valve disposed in the patient circuit between the first end and the second end and configured so as to communicate such a source of breathing gas with an airway of a patient via the patient circuit responsive to the valve being in a first position within the patient circuit and to at least partially restrict communication of such a source of breathing gas with an airway of a patient responsive to the valve being in a second position within the patient circuit, the valve being disposed in the patient circuit and configured such that rotating the valve in a first direction alternatively places the valve in the first position and in the second position; and
   a rotating drive assembly operatively coupled to the valve to rotate the valve in the first direction such that the valve is alternatively disposed in the first position and in the second position;
   a first blower having an inlet and outlet as the source of breathing gas; and
   a second blower having an inlet communicating with ambient atmosphere and an outlet, wherein the valve is adapted to communicate the outlet of the first blower with an airway of a patient and communicates the inlet of the first blower with the outlet of the second blower responsive to the valve being in the first position, and wherein the valve is adapted to communicate the inlet of the first blower with an airway of a patient and communicates the outlet of the first blower with the outlet of the second blower responsive to the valve being in the second position.

2. A high frequency pressure oscillation device according to claim 1, wherein the first blower and the second blower are driven by a common motor.

3. A high frequency pressure oscillation device according to claim 1, wherein the valve includes a generally cylindrical valve member having a first axial surface, a second axial surface, and a side surface, wherein a first hole that extends from the first axial surface to a first portion of the side surface is defined in the cylindrical member, and wherein a second hole that extends from the second axial surface to a second portion of the side surface is also defined in the cylindrical member.

4. A high frequency pressure oscillation device according to claim 3, wherein the first portion of the side surface of the cylindrical valve member and the second portion of the side surface of the cylindrical member are opposite one another.

5. A high frequency pressure oscillation device according to claim 3, wherein the patient circuit includes:

a valve housing having a valve chamber defined therein adapted to receive the cylindrical valve member for rotational movement in the valve chamber, the valve chamber having generally cylindrical side walls, a first end, and a second end;

a first conduit having a first end operatively coupled to the outlet of the first blower and a second end disposed at a first side of the valve chamber;

a second conduit having a first end operatively coupled to the inlet of the first blower and a second end disposed at a second side of the valve chamber;

a third conduit having a first end operatively coupled to the outlet of the second blower and a second end disposed at the first end of the valve chamber; and a fourth conduit having a first end disposed at a second end of the valve chamber and a second end adapted to be coupled to an airway of a patient, so that in the first position, the second end of the first conduit communicates with the first end of the fourth conduit via the first hole through the cylindrical valve member and the second end of the second conduit communicates with the second end of the third conduit via the second hole through the cylindrical valve member, and in the second position, the second end of the second conduit communicates with the first end of the fourth conduit via the first hole through the cylindrical valve member and the second end of the first conduit communicates with the second end of the third conduit via the second hole through the cylindrical valve member.

6. A high frequency pressure oscillation device comprising:

conduit means for communicating a source of breathing gas with an airway of a patient;

valve means for alternatively communicating such a source of breathing gas with an airway of a patient via the conduit means responsive to the valve means being in a first position within the conduit means and for at least partially restricting communication of such a source of breathing gas with an airway of a patient responsive to the valve means being in a second position within the conduit means;

means for rotating the valve means in a first direction such that the valve means is alternatively disposed in the first position and in the second position within the conduit means;

a first blower having an inlet and outlet as the source of breathing gas; and a second blower having an inlet communicating with ambient atmosphere and an outlet, wherein the valve means is adapted to communicate the outlet of the first blower with an airway of a patient and communicates the inlet of the first blower to the outlet of the second blower responsive to the valve means being in the first position, and wherein the valve means is adapted to communicate the inlet of the first blower with an airway of a patient and communicates the outlet of the first blower to the outlet of the second blower responsive to the valve means being in the second position.

7. A method of providing high frequency pressure oscillation comprising:

providing a patient circuit that communicates a source of breathing gas with an airway of a patient;

communicating such a source of breathing gas with an airway of a patient responsive to a valve in the patient circuit being in a first position within the patient circuit;

at least partially restricting communication of such a source of breathing gas with an airway of a patient responsive to the valve being in a second position within the patient circuit;

rotating the valve in a first direction such that the valve is alternatively disposed in the first position and in the second position within the patient circuit;

providing a first blower having an inlet and an outlet as such a source of breathing gas;

providing a second blower having an inlet communicating with ambient atmosphere and an outlet, wherein the communicating step includes communicating the outlet of the first blower with an airway of a patient and communicating the inlet of the first blower to the outlet of the second blower responsive to the valve being in the first position; and communicating the inlet of the first blower with an airway of a patient and communicating the outlet of the first blower to the outlet of the second blower responsive to the valve being in the second position in place of the step of at least partially restricting communication between such a source of breathing gas and an airway of a patient responsive to the valve being in the second position.

* * * * *